(12) United States Patent
Walgreen et al.

(10) Patent No.: US 12,114,995 B2
(45) Date of Patent: Oct. 15, 2024

(54) WIRELESS PRESSURE-SENSITIVE DRESSING ASSEMBLIES AND WIRELESS MONITORING SYSTEMS EQUIPPED THEREWITH

(71) Applicant: Walgreen Health Solutions, Lake Forest, IL (US)

(72) Inventors: Charles R. Walgreen, Lake Forest, IL (US); Sakeena I. Haq, Lake Forest, IL (US)

(73) Assignee: Walgreen Health Solutions, LLC, Evanston, IL (US)

( * ) Notice: Subject to any disclaimer, the term of this patent is extended or adjusted under 35 U.S.C. 154(b) by 787 days.

(21) Appl. No.: 17/241,731

(22) Filed: Apr. 27, 2021

(65) Prior Publication Data

US 2021/0244350 A1 Aug. 12, 2021

Related U.S. Application Data

(60) Continuation-in-part of application No. 16/848,323, filed on Apr. 14, 2020, which is a division of
(Continued)

(51) Int. Cl.
*A61B 5/00* (2006.01)
(52) U.S. Cl.
CPC ............ *A61B 5/447* (2013.01); *A61B 5/0004* (2013.01); *A61B 5/7282* (2013.01);
(Continued)
(58) Field of Classification Search
CPC ..... A61B 5/0004; A61B 5/447; A61B 5/6833; A61B 5/7282; A61B 5/7405; A61B 5/742;
(Continued)

(56) References Cited

U.S. PATENT DOCUMENTS

| 4,503,705 A | 3/1985 | Polchaninoff |
| 4,554,930 A | 11/1985 | Kress |
| (Continued) | | |

FOREIGN PATENT DOCUMENTS

| GB | 2160343 | 12/1985 |
| JP | H08238275 | 9/1996 |
| (Continued) | | |

OTHER PUBLICATIONS

US 9,872,636 B2, 01/2018, Everett et al. (withdrawn)
European Search Report dated May 29, 2018, EP Application No. 15859482.0.

*Primary Examiner* — Kaylee R Wilson
*Assistant Examiner* — Severo Antonio P Lopez
(74) *Attorney, Agent, or Firm* — Hartman Global IP Law; Gary M. Hartman; Domenica N. S. Hartman (57) ABSTRACT

A dressing assembly adapted to be applied on a surface of a patient's body that is susceptible to damage from soft tissue pressure. The dressing assembly includes a carrier having a skin-adhesive film, an outer cover layer overlying and adhered to the skin-adhesive film, an annular-shaped foam member between the skin-adhesive film and the outer cover layer, a cavity defined within the annular-shaped foam member, a lower foam member located within the cavity adjacent a portion of the skin-adhesive film, and a closure assembly overlying the outer cover layer. The closure assembly includes an adhesive element that releasably adheres the closure assembly to the outer cover layer to enable the closure assembly to selectively close and expose the cavity. The closure assembly has an upper form member disposed in the cavity when the closure assembly closes the cavity. A sensor unit is compressed between the lower and upper foam members.

19 Claims, 9 Drawing Sheets

Related U.S. Application Data application No. 14/936,596, filed on Nov. 9, 2015, now Pat. No. 10,638,969.

(60) Provisional application No. 62/077,393, filed on Nov. 10, 2014.

(52) U.S. Cl.
CPC ............ *A61B 5/7405* (2013.01); *A61B 5/742* (2013.01); *A61B 5/746* (2013.01); *A61B 2560/0475* (2013.01); *A61B 2562/0247* (2013.01)

(58) Field of Classification Search
CPC ............ A61B 5/746; A61B 2560/0475; A61B 2562/0247
See application file for complete search history.

(56) References Cited

U.S. PATENT DOCUMENTS

| | | | |
|---|---|---|---|
| 5,253,656 | A | 10/1993 | Rincoe et al. |
| 5,635,201 | A | 6/1997 | Fabo |
| 6,287,253 | B1 | 9/2001 | Ortega et al. |
| 7,090,647 | B2 | 8/2006 | Mimura et al. |
| 7,201,063 | B2 | 4/2007 | Taylor |
| 7,378,975 | B1 | 5/2008 | Smith et al. |
| 8,011,041 | B2 | 9/2011 | Hann |
| 8,393,229 | B2 | 3/2013 | Tao et al. |
| 8,535,246 | B2 | 9/2013 | Drennan et al. |
| 8,558,702 | B2 | 10/2013 | Smith et al. |
| 8,675,059 | B2 | 3/2014 | Johnson et al. |
| 8,840,573 | B2 | 9/2014 | Neustaedter et al. |
| 8,997,588 | B2 | 4/2015 | Taylor |
| 9,135,804 | B2 | 9/2015 | Hann |
| 9,149,211 | B2 | 10/2015 | Mravyan et al. |
| 9,271,665 | B2 | 3/2016 | Sarrafzadeh et al. |
| 9,320,665 | B2 | 4/2016 | Main et al. |
| 9,574,955 | B2 | 2/2017 | Iwase et al. |
| 9,778,131 | B2 | 10/2017 | Everett et al. |
| 9,814,637 | B2 | 11/2017 | Sazonov |
| 10,004,428 | B2 | 6/2018 | Everett et al. |
| 10,140,837 | B2 | 11/2018 | Shen et al. |
| 10,251,593 | B2 | 4/2019 | Sugla et al. |
| 10,297,143 | B1 | 5/2019 | Giffen et al. |
| 10,357,197 | B2 | 7/2019 | Smith, Jr. et al. |
| 10,383,527 | B2 | 8/2019 | Ai-Ali |
| 10,492,734 | B2 | 12/2019 | Ferber |
| 10,535,432 | B2 | 1/2020 | Perlman et al. |
| 2005/0131318 | A1 | 6/2005 | Peifer et al. |
| 2005/0228317 | A1 | 10/2005 | Mathews |
| 2008/0208063 | A1 | 8/2008 | Brauers et al. |
| 2008/0312574 | A1 | 12/2008 | Perot |
| 2009/0056020 | A1* | 3/2009 | Caminade ............ G01L 1/205 5/713 |
| 2009/0209830 | A1 | 8/2009 | Nagle et al. |
| 2011/0263950 | A1 | 10/2011 | Larson et al. |
| 2012/0277637 | A1 | 11/2012 | Vahdatpour et al. |
| 2013/0090571 | A1 | 4/2013 | Nourani et al. |
| 2013/0317393 | A1 | 11/2013 | Weiss et al. |
| 2014/0039351 | A1 | 2/2014 | Mix et al. |
| 2014/0243709 | A1 | 8/2014 | Gibson et al. |
| 2014/0343889 | A1 | 11/2014 | Ben Shalom et al. |
| 2015/0045630 | A1 | 2/2015 | Poliakine-Baruchi et al. |
| 2015/0094618 | A1 | 4/2015 | Russell et al. |
| 2015/0173667 | A1 | 6/2015 | Ben Shalom et al. |
| 2015/0320352 | A1 | 11/2015 | Ben Shalom et al. |
| 2017/0115171 | A1 | 4/2017 | Huang et al. |
| 2018/0014774 | A1 | 1/2018 | Hollopeter et al. |
| 2018/0146913 | A1 | 5/2018 | Kaikenger et al. |
| 2018/0255879 | A1 | 9/2018 | Taryma et al. |
| 2019/0021650 | A1 | 1/2019 | Lee et al. |
| 2019/0049322 | A1 | 2/2019 | James et al. |
| 2019/0104982 | A1 | 4/2019 | Dunn et al. |
| 2019/0231228 | A1 | 8/2019 | Larson et al. |
| 2019/0374133 | A1 | 12/2019 | Shen et al. |

FOREIGN PATENT DOCUMENTS

| | | |
|---|---|---|
| WO | 2007106040 | 9/2007 |
| WO | 2011113070 | 9/2011 |
| WO | 2015175317 | 11/2015 |
| WO | 2017176667 | 10/2017 |
| WO | 2017218725 | 12/2017 |
| WO | 2018130824 | 7/2018 |
| WO | 2019060250 | 3/2019 |
| WO | 2019240569 | 12/2019 |

* cited by examiner

WIRELESS PRESSURE-SENSITIVE DRESSING ASSEMBLIES AND WIRELESS MONITORING SYSTEMS EQUIPPED THEREWITH

CROSS-REFERENCE TO RELATED APPLICATIONS

This is a continuation-in-part patent application of co-pending U.S. patent application Ser. No. 16/848,323 filed Apr. 14, 2020, which is a division of U.S. patent application Ser. No. 14/936,596 filed Nov. 9, 2015 (now U.S. Pat. No. 10,638,969), which claims the benefit of U.S. patent application Ser. No. 62/077,393 filed Nov. 10, 2014. The contents of these prior applications are incorporated herein by reference.

BACKGROUND OF THE INVENTION

The present invention generally relates to products for use with health care patients. More particularly, the present invention encompasses dressing assemblies capable of providing protection to skin areas at risk of pressure ulcers as well as skin areas with existing pressure ulcers, wounds, surgical incisions, and/or skin ailments, and to such dressing assemblies that are capable of accommodating sensors to monitor soft tissue pressure for use by patient monitoring systems.

Pressure (decubitus) ulcers, commonly known as bedsores, present a serious problem to bedridden and wheelchair-confined patients. Prolonged pressure from a patient's body weight on a bony prominence is the most common cause of pressure ulcers. Prevention of and care for a preexisting pressure ulcer typically include treatment plans that involve relieving pressure on the exposed area by positioning and maintaining the patient off susceptible areas and any preexisting pressure ulcers, and minimizing localized pressure through the use of gel pads and similar types of products capable of absorbing and/or distributing pressure. However, such approaches can be insufficient if caregivers are unaware that a patient has shifted his/her weight onto prominences and sensitive areas that are prone to pressure ulcers.

There are a wide variety of pressure sensors in the industrial and medical markets, some of which have found use to monitor pressure ulcers. Notable examples include those that use air and fluid displacement techniques, as well as electromechanical analog devices. Many of these sensors are very portable and can be used to measure pressures at various locations of a patient at any point in time.

Conventional dressing assemblies often used with pressure sensors include a simple multilayer construction dressing with a sensor embedded therebetween. These conventional dressing assemblies are hardwired using a connection cable connected to the sensor on one end of the cable and to a controller on the other end of the cable. The controller is strapped to a bed to monitor a patient and alert a patient or caregiver that soft tissue pressure has exceeded some predetermined level that over time may lead to pressure ulcers. These dressing assemblies are often impaired in their effectiveness because they do not adequately secure their sensor in position, especially if the patient is frequently shifting their position in bed. Therefore, the construction of the dressing assembly is often based on trying to reduce the thickness profile of the dressing as much as possible to decrease the possibility of the dressing shifting as the patient moves into a different position. However, very thin dressing assemblies may sacrifice patient comfort resulting in patients trying to reposition the dressing assemblies themselves. Additionally, very thin dressing assemblies may allow the sensor to apply excessive pressure to the skin if not adequately cushioned.

There are certain problems, shortcomings, or disadvantages associated with existing dressing assemblies, and it would be desirable if improved dressing assemblies were available that were capable of being applied to and protecting skin at various anatomical sites, especially at bony prominences, and were configured to avoid or reduce soft tissue pressure at such sites to reduce the risk of tissue damage including pressure ulcers. Also needed is for such dressing assemblies to be adapted to accommodate pressure sensors to provide a pressure monitoring capability while still capable of avoiding or reducing soft tissue pressure.

SUMMARY OF THE INVENTION

The present invention provides a dressing assembly adapted to be applied on or near a surface of the patient's body that is susceptible to damage from soft tissue pressure. The dressing assembly is preferably a wireless pressure-sensitive dressing assembly capable of use in a wireless monitoring system to provide a warning to a patient or caregiver that the patient should be moved to reduce the risk of soft tissue damage to the patient.

According to one aspect of the invention, a wireless pressure-sensitive dressing assembly includes a carrier that has a skin-adhesive film, an outer cover layer overlying and adhered to the skin-adhesive film, an annular-shaped foam member between the skin-adhesive film and the outer cover layer, a cavity defined within the annular-shaped foam member, a lower foam member located within the cavity adjacent a portion of the skin-adhesive film, and a closure assembly overlying the outer cover layer. The closure assembly includes a nonpermanent adhesive element that releasably adheres the closure assembly to the outer cover layer to enable the closure assembly to selectively close and selectively expose the cavity. The closure assembly has an upper form member that is disposed in the cavity when the closure assembly releasably closes the cavity. The dressing assembly further includes a sensor unit removably secured within the cavity and compressed between the lower and upper foam members. The sensor unit generates electrical outputs corresponding to soft tissue pressure sensed by the wireless pressure-sensitive dressing assembly at the surface of the patient's body.

According to other aspects of the invention, methods are provided that make use of dressing assemblies comprising the elements described above. Such a method may entail exposing the cavity with the closure assembly, placing a sensor unit within the cavity and closing the cavity with the closure assembly to compress the sensor unit between the lower and upper foam members, generating electrical outputs with the sensor unit corresponding to soft tissue pressure sensed by the sensor unit at the surface of the patient's body, monitoring the electrical outputs generated by the sensor unit, and generating an alert if the electrical outputs exceed a threshold level.

Other aspects and advantages of this invention will be appreciated from the following detailed description.

DETAILED DESCRIPTION OF THE INVENTION

Various features and advantages of certain dressing assemblies and sensor units are explained in the following description with reference to nonlimiting embodiments that are illustrated in the accompanying drawings. Descriptions of well-known materials, processing techniques, components and equipment are omitted so as not to unnecessarily obscure the invention in detail. It should be understood, however, that the detailed description and the specific examples, while describing certain embodiments of the invention, are given by way of illustration only and not by way of limitation. Various substitutions, modifications, additions and/or rearrangements within the spirit and/or scope of the invention will become apparent to those skilled in the art from the drawings, detailed description, and examples.

Figure 1:
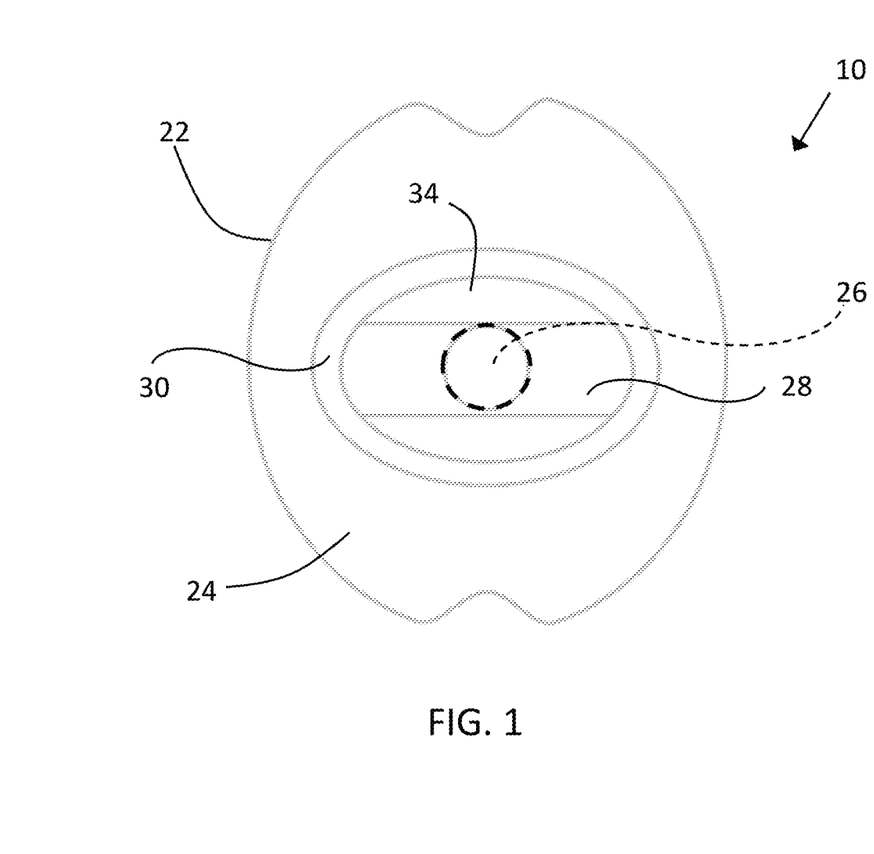
FIG. 1 schematically represents a plan view of a dressing assembly in accordance with a first nonlimiting embodiment of the invention.
Figure 2:
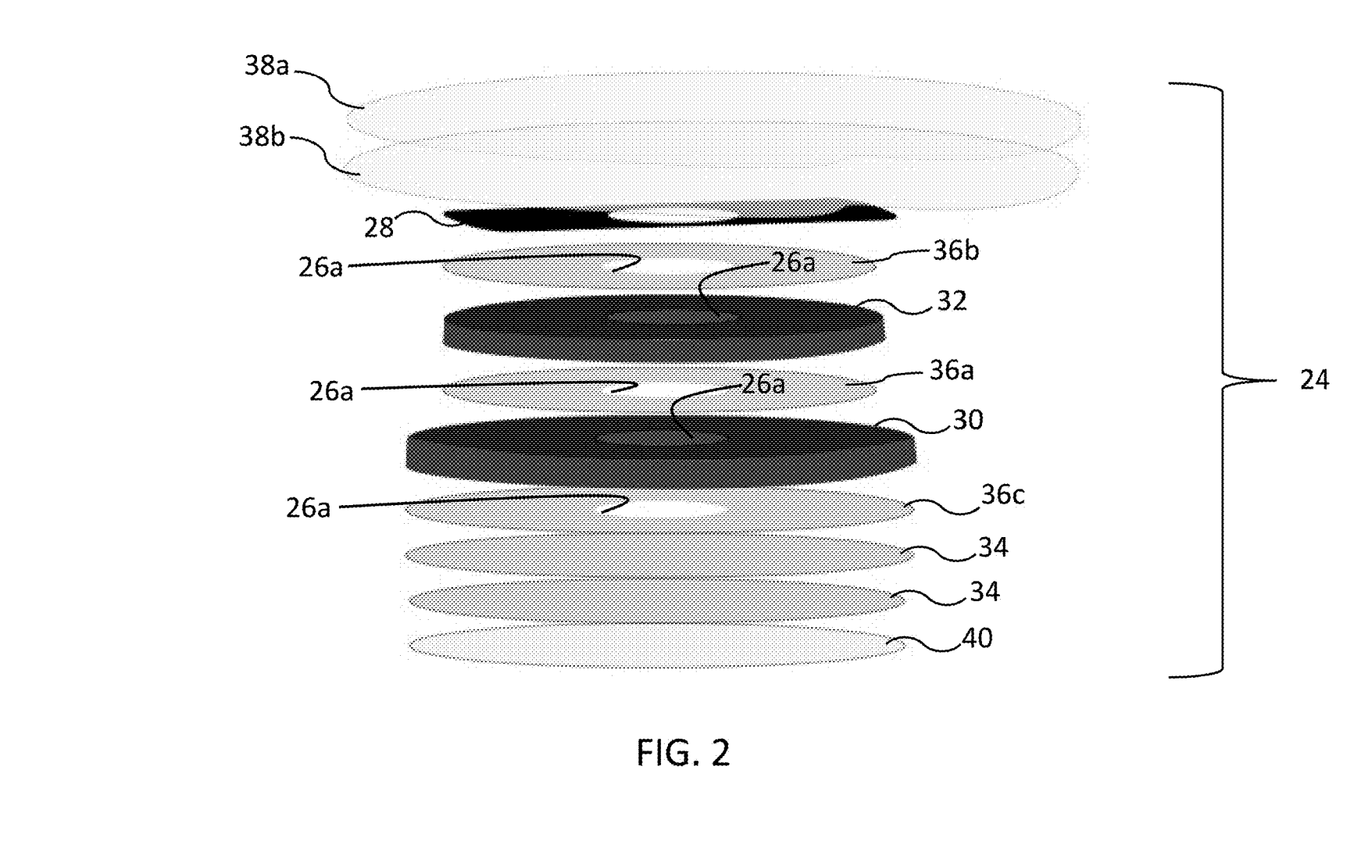
FIG. 2 schematically represents an exploded view of the dressing assembly of FIG. 1.
Figure 3:
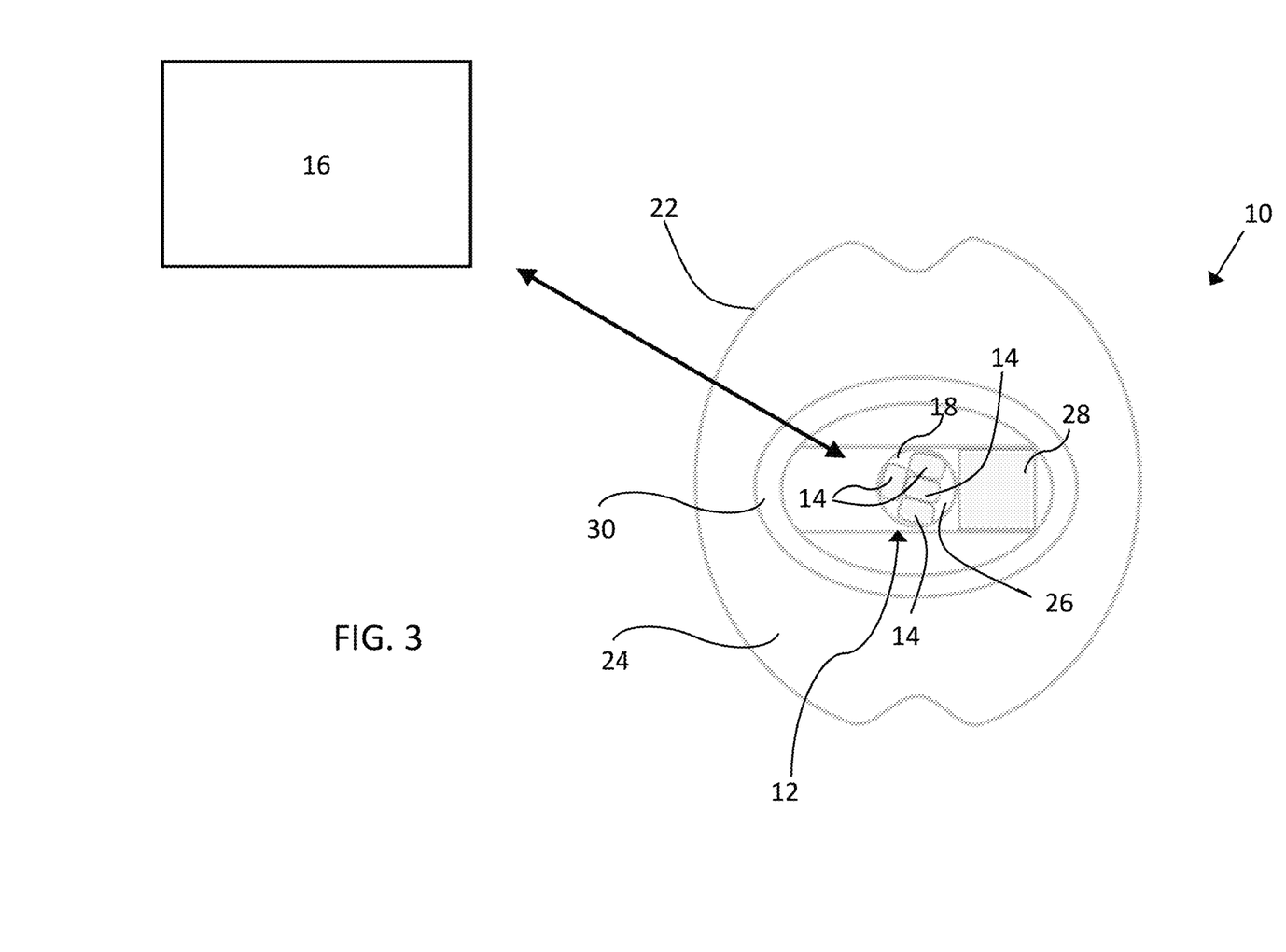
FIG. 3 schematically represents the dressing assembly of FIGS. 1 and 2 equipped with a pressure sensing unit and as a component of a wireless monitoring system in accordance with a nonlimiting aspect of the invention.

The present invention provides dressing assemblies 10 that are adapted to be applied and adhesively secured to the skin of an individual at various anatomical sites, especially at bony prominences, and are configured to protect the skin and reduce soft tissue pressure at such sites to avoid or reduce the risk of tissue damage, as a nonlimiting example, pressure ulcers. A nonlimiting embodiment of a dressing assembly is represented in FIGS. 1 through 3, and is depicted in FIG. 3 as accommodating a sensing unit 12 that comprises one or more transducers 14, as nonlimiting examples, devices capable of measuring parameters such as pressure, temperature, moisture, etc. This and other dressing assemblies 10 disclosed herein in which one or more transducers 14 are pressure-sensitive transducers 14 may be referred to as pressure-sensitive dressing assemblies 10. Furthermore, the dressing assemblies 10 may be utilized as part of a monitoring system configured to monitor a patient. As a nonlimiting example, such a system may comprise a processing device 16 (FIG. 3), for example, a tablet, a smartphone, a gateway, a server, or a wireless converter box. The sensing units 12 of the dressing assemblies 10 can be equipped to wirelessly communicate with the processing device 16, as schematically represented in FIG. 3, in which case the dressing assemblies 10 and monitoring system may be further described as "wireless."

If a dressing assembly 10 is equipped with pressure-sensitive transducers 14 as part of a pressure monitoring system, a function of the system may be to monitor a patient that is reclined or otherwise in a position that may result in the patient's weight applying pressure to an area of the patient's body that is susceptible to pressure ulcers, such as soft tissue overlying a bony prominence. Such a pressure monitoring system may further operate to correlate soft tissue pressure levels with time to warn if an applied pressure has met certain pressure and time thresholds that, in combination, are likely to result in or exacerbate a pressure ulcer. Suitable operating techniques and algorithms with this capability are disclosed in U.S. Pat. Nos. 8,535,246 and 10,638,969, whose contents are incorporated herein by reference.

FIG. 3 schematically represents multiple pressure-sensitive transducers 14 of the sensing unit 12 mounted to a substrate 18. The term "pressure-sensitive" is used herein to refer to a transducer that measures or otherwise produces an output indicative of or in response to pressure or force applied to the transducer. The construction and arrangement of the dressing assembly 10, sensing unit 12, and its transducers 14 determine the sensitivity of the sensing unit 12. Though the use of various types of pressure-sensitive transducers is possible, in practice particularly suitable results have been obtained with dome switches. As used herein, a dome switch operates by closing and generating an output only when a pressure or force applied to the switch meets a predetermined threshold. In practice, the predetermined threshold of each transducer 14 is selected to be a level that, preferably in combination with predetermined time thresholds, is likely to result in or exacerbate a pressure ulcer. In this manner, if a predetermined threshold is met at at least one of the transducers 14, the sensing unit 12 can generate a signal to alert a patient and/or their caregiver(s) so that the patient moves or can be moved in such a way as to relieve pressure from the sensing unit 12. Additional transducers may be mounted to the substrate 18, including sensors for monitoring temperature, moisture, capillary flow, skin resistivity, and other biological indicators. A battery or other power source (not shown) for powering the pressure-sensitive transducers 14 and any optional transducers may be incorporated into the sensing unit 12, for example, on the substrate 18.

The dressing assembly 10 represented in FIGS. 1 through 3 has a round outer periphery 22 defined by a carrier 24, within which a central cavity 26 is defined and sized to accommodate the sensing unit 12 (FIG. 3). The dressing assembly 10 further comprises a strip 28 that releasably overlies the cavity 26, can be peeled back to allow placement of the sensing unit 12 in the cavity 26, and then reapplied over the cavity 26 to temporarily secure the sensing unit 12 within the cavity 26. The dressing assembly 10 and its outer periphery 22 are preferably sized and shaped for the particular anatomic location on the patient where the dressing assembly 10 will be located. As such, alternative shapes may be used and preferred for the dressing assembly 10.

As seen in FIG. 2, the carrier 24 of the dressing assembly 10 may be constructed to comprise first (inner) and second (outer) foam layers 30 and 32 embedded between inner layers 34 and interior layers 36a-c of additional dressing materials, which may be formed of a foam, hydrocolloid, alginate self-adherent dressing or other suitable materials. FIG. 2 shows the inner layers 34, the innermost interior layer 36c, and the inner foam layer 30 as approximately the same size, and the center interior layer 36a (between the inner and outer foam layers 30 and 32), the outer foam layer 32, and the outermost interior layer 36b as approximately the same size but smaller than the inner layers 34, the innermost interior layer 36c, and the inner foam layer 30. At least one cover layer 38a and/or 38b overlies and is larger than all of the layers 30, 32, 34, and 36a-c. The cavity 26 in FIGS. 1 and 3 is represented in FIG. 2 as defined by an aligned series of apertures or openings 26a formed within certain layers of the dressing assembly 10 to be approximately equally in size to accommodate the sensing unit 12, including its transducers 14 and substrate 18. The openings 26a are formed in the inner and outer foam layers 30 and 32 and at least the outermost interior layer 36b and the center interior layer 36a between the inner and outer foam layers 30 and 32. The openings 26a may also be defined in the innermost interior layer 36c of the carrier 24 so that the sensing unit 12 can be placed in closer proximity to a patient's skin. In the case of an open wound, openings are preferably not present in all of the inner layers 34 of the carrier 24 so that at least one inner layer 34 is present between the sensing unit 12 and the open wound. The lowermost inner layer 34 directly facing the patient's skin is preferably a non-adhesive foam or absorbent material without an opening formed therein.

A lowermost skin-facing adhesive layer 40 of the carrier 24 is positioned within the carrier 24 so as to directly face and contact the patient's skin when the carrier is applied to the skin. The skin-facing adhesive layer 40 includes an adhesive that covers its entire lower surface or is located along the periphery 22 of the carrier 24 to adhere the dressing assembly 10 to the skin. The adhesive is preferably a medical grade adhesive and hypoallergenic so as not to damage the skin, for example, a soft silicone or hydrogel. If the dressing assembly 10 is to be used for wound coverage, the adhesive is preferably located only along the periphery 22 of the carrier 24, with the remaining surface of the skin-facing adhesive layer 40 being an absorbent foam/fabric.

The outer surface of the cover layer 38a may be a smooth tricot material to reduce friction and shear. The dressing assembly 10 preferably allows for heat and humidity transfer. For this purpose, the foam layers 30 and 32 may be highly porous for heat and moisture dissipation. Layers of the carrier 24 may also be perforated to enable medications to pass therethrough. For example, the layer 34 and the skin-facing adhesive layer 40 may be perforated so that medications can be actively or passively applied from within the cavity 26.

A significant feature of dressing assemblies 10 described herein is believed to be the ability of the dressing assemblies 10 to securely hold a sensing unit 12 within the cavity 26 so as to be in close proximity to the skin of a patient, and yet be removable from the carrier 24 and replaceable. For this purpose, the cover layer 38b and the outermost interior layer 36b are preferably adhesive layers, and the strip 28 is a nonadhesive layer (for example, formed of a polyester) between the cover layer 38b and the outermost interior layer 36b that enables the cover layers 38a and 38b to be at least partially detached from the remainder of the carrier 24 to expose the cavity 26 formed by the series of openings 26a.

Figure 4:
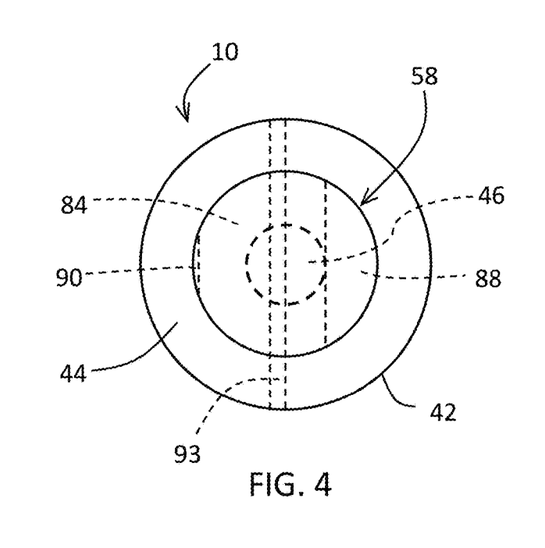
FIGS. 4, 5, and 6 schematically represent plan views of dressing assemblies in accordance with second, third, and fourth nonlimiting embodiments of the invention.
Figure 5:
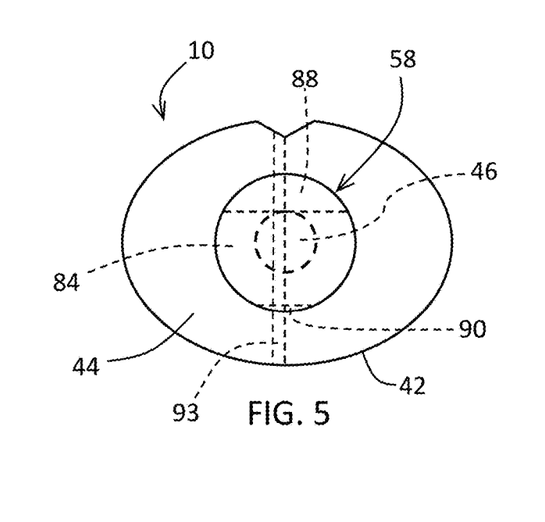
Figure 6:
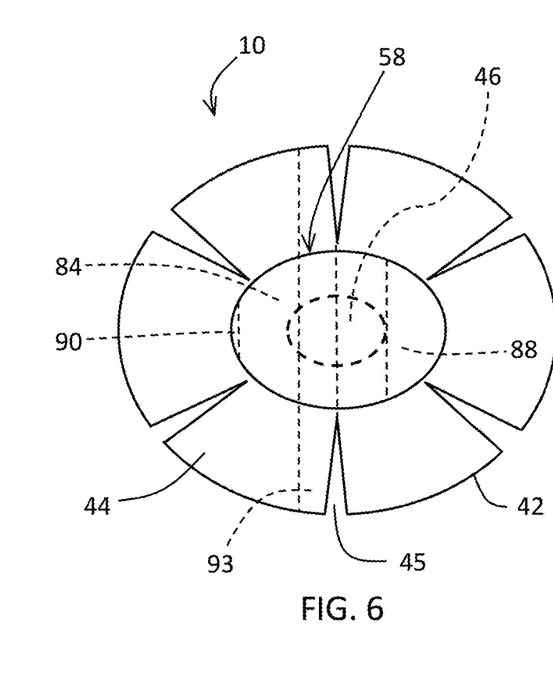

Suitable shapes and sizes for a particular dressing assembly 10 will depend on which anatomic site the assembly 10 is to be applied and the thickness of the sensing unit 12. FIGS. 4 through 6 represent further embodiments of dressing assemblies 10 having shapes and sizes that accommodate different anatomic sites, including the sacrum/coccyx, heel/elbow, and spine/outer hip/ischium areas. For convenience, consistent reference numbers are used in FIGS. 4 through 6 to identify certain features of the dressing assemblies 10 that have the same function or are functionally related or equivalent. Though not intending to be so limited, the dressing assembly 10 of FIG. 4 has a circular periphery 42 defined by a carrier 44 and is configured for general use as a dressing for a variety of anatomic sites, the dressing assembly 10 of FIG. 5 has an oval periphery 42 defined by its carrier 44 and is particularly configured for use as a sacral dressing for application over the sacrum, and the dressing assembly 10 of FIG. 6 has radial slits 45 along an oval periphery 42 of its carrier 44 such that the assembly 10 is particularly configured for use as a dressing for application over relatively large protuberances, for example, bony prominences such as the heel and elbow. Within the carrier 44 of each dressing assembly 10 shown in FIGS. 4 through 6, a central cavity 46 is defined and sized to accommodate a sensing unit 12, such as of a type described above in reference to FIGS. 1 through 3 or described in the following discussion of FIGS. 7A through 10. In addition to accommodating the thickness of the sensing unit 12, the thicknesses of the carriers 44 of the dressing assemblies 10 of FIGS. 4 through 6 are preferably two to three times the thickness of the sensing unit 12 to promote the dissemination of the focal pressure of the sensing unit 12 that might otherwise be transmitted to the skin and potentially lead to soft tissue pressure damage.

The dressing assemblies 10 of FIGS. 4 through 6 are capable of sharing a similar construction. FIGS. 7A-C and 8 schematically represent the construction of the dressing assembly 10 of FIG. 4, though it should be understood that the construction represented in FIGS. 7A-C and 8 is also applicable to the dressing assemblies 10 of FIGS. 5 and 6. It should be noted that FIGS. 4 through 8 are drawn for purposes of clarity when viewed in combination with the following description, and therefore are not necessarily to scale.

Figure 7A:
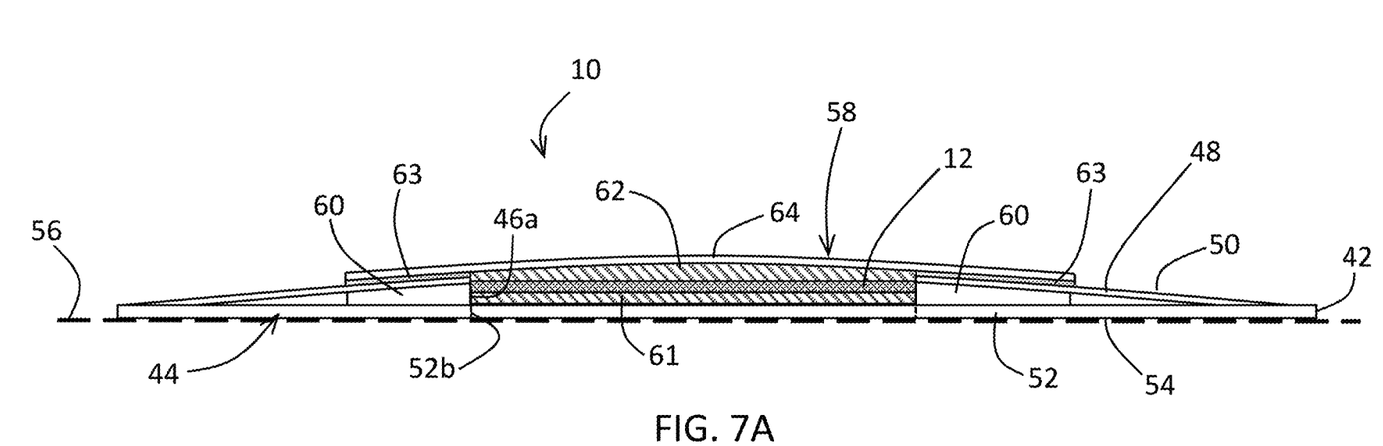
FIG. 7A schematically represents a cross-sectional view of the dressing assembly of FIG. 4 with a sensor unit placed in a cavity between a closure assembly at an outward-facing side of the dressing assembly and a skin-adhesive layer at a skin-facing side of the dressing assembly so that the skin-adhesive layer is between the sensor unit and the skin of an individual to which the dressing assembly has been applied.

FIG. 7A schematically represents a cross-sectional view of the dressing assembly 10 of FIG. 4 with a sensor unit 12 placed in its cavity 46 (labeled in FIGS. 7B and 7C) between an outer cover layer 48 at an outward-facing surface or side 50 of the dressing assembly 10 and a skin-adhesive film 52 at a skin-facing surface or side 54 of the dressing assembly 10 so that the skin-adhesive film 52 is between the sensor unit 12 and the skin 56 of an individual to which the dressing assembly 10 has been applied. The dressing assembly 10 further comprises a closure assembly 58 that releasably overlies the cavity 46 and closes an opening 68 (FIG. 7C) to the cavity 46 formed by a central aperture 48a in the outer cover layer 48. The closure assembly 58 can be peeled back or completely removed to allow placement of the sensing unit 12 in the cavity 46, and then reapplied over the cavity 46 to temporarily secure the sensing unit 12 within the cavity 46. The cavity 46 is primarily defined by a central aperture 46a formed in an annular-shaped foam member 60 of the carrier 44, which is substantially and preferably completely encased between the outer cover layer 48 and the skin-adhesive film 52, for example, as a result of the perimeters of the outer cover layer 48 and the skin-adhesive film 52 being bonded together to form the periphery 42 of the carrier 44. The carrier 44 comprises second (lower) and third (upper) foam members 61 and 62 that together can be entirely contained within the cavity 46. As shown in FIG. 7A, the lower foam member 61 is within a lower region of the cavity 46 and immediately adjacent the upper surface of the skin-adhesive film 52, and the upper foam member 62 is within an upper region of the cavity 46 and immediately adjacent a cover 64 of the closure assembly 58. Both foam members 61 and 62 may be identically sized and shaped such that the entire perimeter of each contacts or is adjacent to the wall of the aperture 46a in the foam member 60. The upper foam member 62 is centrally located on and bonded to the cover 64 and surrounded by a nonpermanent adhesive element 63 that releasably secures the closure assembly 58 to the outer cover layer 48. As a result, the adhesive element 63 of the closure assembly 58 positions and secures the upper foam member 62 within the upper region of the cavity 46 as a result of the upper foam member 62 protruding downward into the cavity 46 from the cover 64. In addition, the adhesive element 63 enables the upper foam member 62 to be removed from the cavity 46 as part of the closure assembly 58 when the latter is peeled back or completely removed from the remainder of the carrier 44 (FIG. 7C).

The foam members 61 and 62 received in the cavity 46 have thicknesses that are preferably sufficient so that the sensor unit 12, when placed on the lower foam member 61 in the cavity 46, is secured within the cavity 46 as a result of the upper foam member 62 being compressed between the sensor unit 12 and the cover 64 and/or the lower foam member 61 being compressed between the sensor unit 12 and the skin-adhesive film 52. For this purpose, the foam members 61 and 62 may have a combined thickness roughly equal to the thickness of the foam member 60. In combination, the foam members 60, 61, and 62 provide a pressure-absorbing and disseminating structure within the dressing assembly 10 that extends radially outward beyond the cavity 46 and the sensor unit 12 within the cavity 46 to distribute externally applied pressure that might otherwise be transmitted from the user's environment (as nonlimiting examples, the bed of a bedridden patient or the wheelchair of a wheelchair-confined patient) to the skin 56 and potentially lead to soft tissue pressure damage.

Figure 7B:
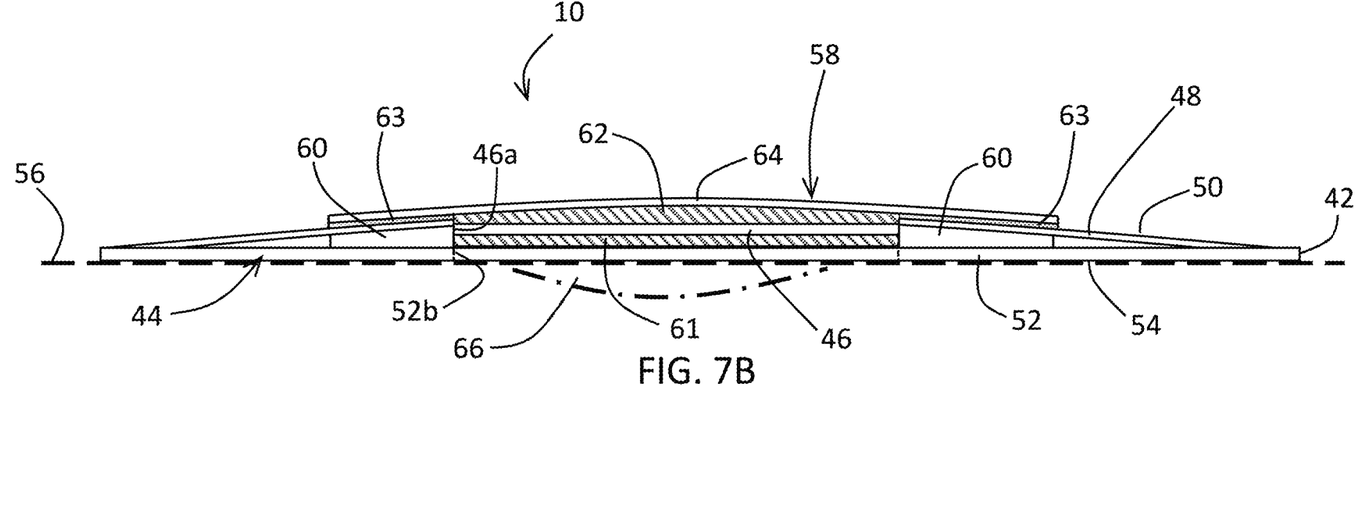
FIG. 7B schematically represents a cross-sectional view of the dressing assembly of FIG. 7A with the sensor unit removed from the cavity between the closure assembly and the skin-adhesive layer of the dressing assembly.

FIG. 7B is a cross-sectional view of the dressing assembly 10 of FIG. 7A after the sensor unit 12 has been removed from the cavity 46. In this configuration, the dressing assembly 10 does not have any sensing function, and instead can be beneficially used as a wound dressing that applies very little pressure to a pre-existing wound 66 at the surface of the skin 56 directly beneath the cavity 46. The closure assembly 58 closes the cavity 46 at the outward-facing side 50 of the dressing assembly 10 and its upper foam member 62 can be forced into the cavity 46 by an external pressures without transmitting that pressure to the user's skin 56 and, if present, the wound 66. The annular-shaped foam member 60 continues to distribute external pressure around the cavity 46 that might otherwise be transmitted from the user's environment to the user's skin 56 and, if present, the wound 66.

Figure 7C:
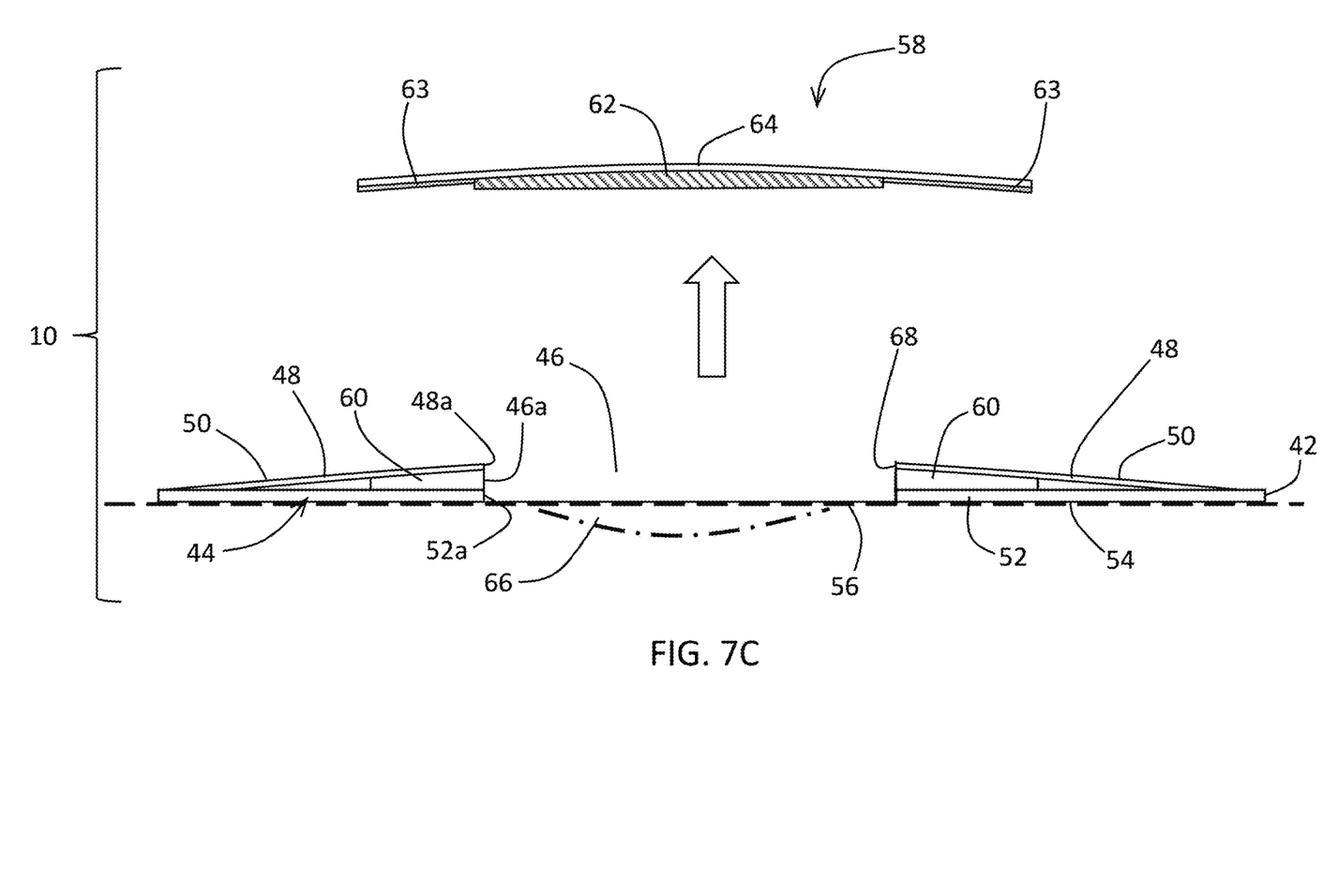
FIG. 7C schematically represents a cross-sectional view of the dressing assembly of FIG. 7B with the closure assembly and the skin-adhesive layer removed so that the cavity is exposed at the outward-facing side of the dressing assembly and is continuous to the surface of the individual's skin through an aperture created in the skin-adhesive layer.

FIG. 7C is a cross-sectional view of the dressing assembly 10 of FIGS. 7A and 7B with the closure assembly 58 completely removed to expose the cavity 46 and its opening 68 at the outward-facing side 50 of the dressing assembly 10. Additionally, the cavity 46 is shown as continuous to the surface of the individual's skin 56 through an aperture 52a created in the skin-adhesive film 52. The aperture 52a may be selectively formed in the skin-adhesive film 52 as a result of the skin-adhesive film 52 having a line of weakness, for example, perforations 52b (FIGS. 7A and 7B) so that a central portion of the skin-adhesive film 52 surrounded by the perforations 52b can be manually removed without otherwise damaging the film 52. As schematically represented in FIG. 7C, the creation of the aperture 52a in the skin-adhesive film 52 results in the cavity 46 defining a through-hole entirely through the carrier 44, which has the beneficial effect of avoiding contact between the dressing assembly 10 and a pre-existing wound 66 at the surface of the skin 56 exposed within the cavity 46. As evident from FIG. 7C, removal of the closure assembly 58 has the beneficial effect of exposing the wound 66 to air. Alternatively, it is foreseeable that the closure assembly 58 could be reapplied to prevent ingress of foreign matter and/or assist in retaining a medication placed on the wound 66.

Figure 8:
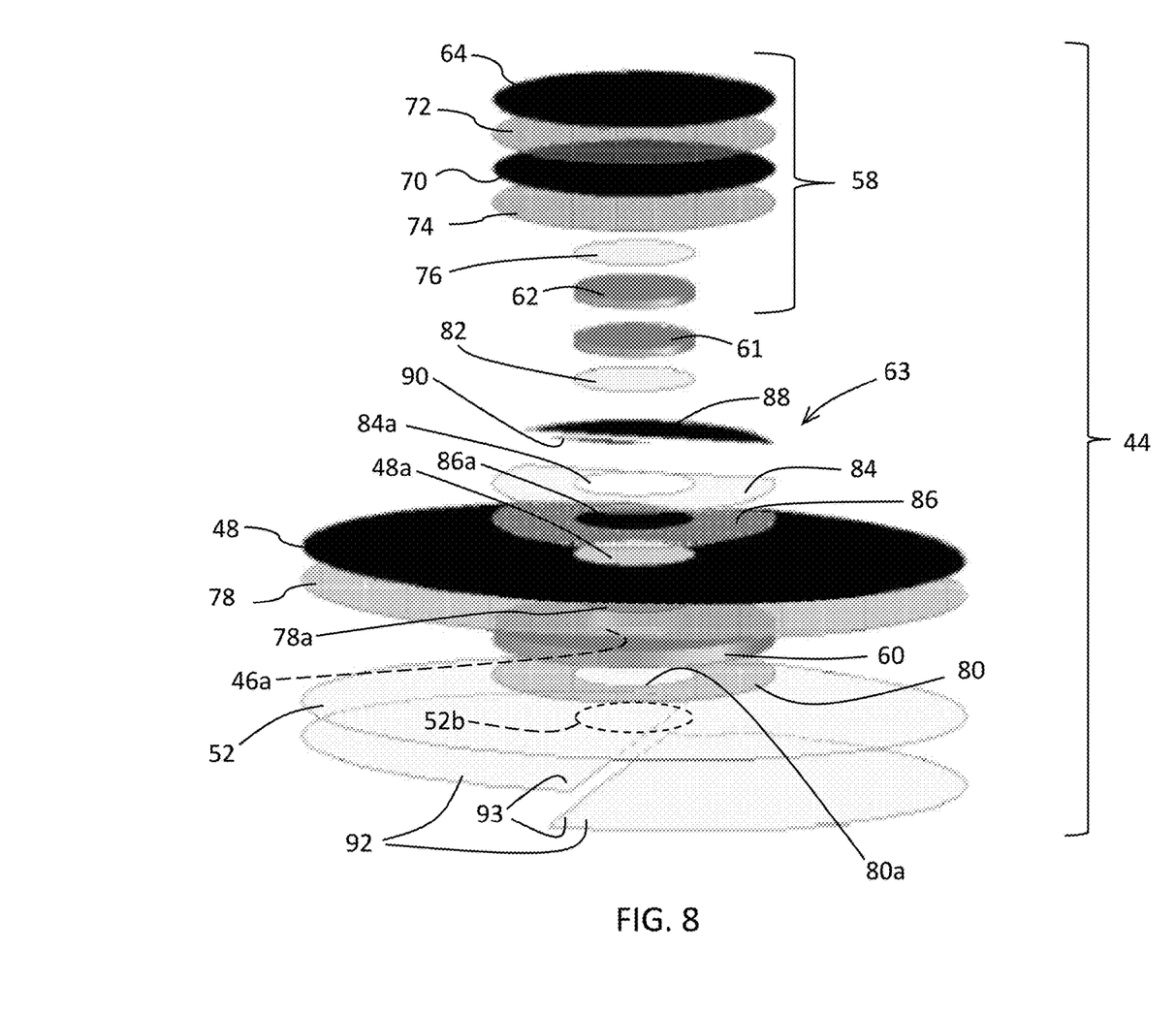
FIG. 8 schematically represents an exploded view of the dressing assembly of FIGS. 4 and 7A through 7C.

FIG. 8 schematically represents a nonlimiting example of individual layers of materials that can be combined to construct the carrier 44 schematically represented in FIGS. 7A-C. As represented, the closure assembly 58 can be constructed to include a support film 70 having the same peripheral size and shape as the cover 64 and bonded to the cover 64 with an adhesive film 72, for example, a pressure-sensitive adhesive (PSA) film. Two additional adhesive films 74 and 76 are shown as adhering the upper foam member 62 to the support film 70 opposite the cover 64. In combination, the upper foam member 62, cover 64, support film 70, and adhesive films 72, 74, and 76 are represented in FIG. 8 as forming the closure assembly 58. The adhesive films 72 and 74 roughly have the same peripheral size and shape as the cover 64 and support film 70, and the adhesive film 76 roughly has the same peripheral size and shape as the upper foam member 62. The adhesive film 74 is larger than and extends radially beyond the upper foam member 62 to serve as a component of the aforementioned adhesive element 63 that releasably secures the closure assembly 58 to the outer cover layer 48, as will be discussed in more detail below.

FIG. 8 shows the outer cover layer 48 and the skin-adhesive film 52 as having the same peripheral size and shape and bonded together with an adhesive film 78 that also roughly has the same peripheral size and shape as the outer cover layer 48 and the skin-adhesive film 52. Additionally, the adhesive film 78 has a central aperture 78a roughly having the same peripheral size and shape as the aperture 48a in the outer cover layer 48 and the central portion of the skin-adhesive film 52 surrounded by the perforations 52b. The adhesive film 78 also bonds the foam member 60 to the lower surface of the outer cover layer 48, and the foam member 60 is further bonded to the upper surface of the skin-adhesive film 52 with another adhesive film 80 that roughly has the same peripheral size and shape as the foam member 60. The adhesive film 80 also has an aperture 80a that is roughly the same peripheral size and shape as the aperture 46a in the foam member 60 so that anything placed in the cavity 46 will not be adhered to the skin-adhesive film 52 by the adhesive film 80.

When placed in the cavity 46, the lower foam member 61 is bonded to the upper surface of the skin-adhesive film 52 with an adhesive film 82 that roughly has the same peripheral size and shape as the lower foam member 61. No adhesive is required between the foam members 61 and 62, such that a sensor unit 12 placed in the cavity 46 is not adhered to any surface within the cavity 46 and any contact between the foam members 61 and 62 does not interfere with the removal of the closure assembly 58 from the outward-facing side 50 of the dressing assembly 10 or the removal of the sensor unit 12 from the cavity 46. As such, the sensor unit 12 can be removed from the carrier 44 for use in a different carrier, or the sensor unit 12 in the carrier 44 can be replaced with a different sensor unit. Other than limitations of peripheral size and thickness (which are established by the foam member 60 and the cavity 46 it defines), essentially any sensor unit can be accommodated by the carrier 44.

To facilitate the attachment and removal of the closure assembly 58 at the outward-facing side 50 of the carrier 44 defined by the outer cover layer 48, the nonpermanent adhesive element 63 previously described preferably comprises multiple components. In FIG. 8, the nonpermanent adhesive element 63 includes a structural film 84 bonded with an adhesive film 86 to the surface of the outer cover layer 48 surrounding its aperture 48a. The structural film 84 and the adhesive film 86 have peripheral sizes and/or shapes that are different from the adhesive film 74 of the closure assembly 58. Additionally, the structural film 84 and the adhesive film 86 each have a central aperture 84a and 86a, respectively, that has roughly the same peripheral size and shape as the apertures 46a, 48a, 78a, and 80a of the foam member 60, outer cover layer 48, and adhesive films 78 and 80 so that in combination these apertures 46a, 48a, 78a, 80a, 84a, and 86a are coaxially aligned to ensure continuity of the cavity 46.

FIG. 8 further represents the structural film 84 and the adhesive film 86 as each having a circular outer periphery with the exception of a circular segment, which accommodates a circular segment-shaped adhesive film 88 that secures the adhesive film 74 of the closure assembly 58 directly to the outer cover layer 48. The carrier 44 further comprises a nonadhesive film 90 bonded to the adhesion film 74 and located between the adhesive film 74 and the structural film 84 spaced apart from the adhesive film 88, providing a grip tab by which the adhesion provided by the adhesion film 74 between the closure assembly 58 and the outer cover layer 48 can be overcome by lifting grip tab and peeling the closure assembly 58 back from the outer cover layer 48.

The skin-adhesive film 52 is the only member of the carrier 44 that is intended to contact the skin of a patient. As such, the skin-adhesive film 52 is preferably formed of materials that do not cause skin irritation or a delayed-type hypersensitivity. Suitable but not limiting materials for this purpose are a thermoplastic elastomer (TPE) tape with a silicone adhesive on its lower surface. FIG. 8 represents the carrier 44 as further comprising a liner 92 that covers the lower surface of the skin-adhesive film 52 to preserve its adhesive function until the carrier 44 is to be applied to a patient. The liner 92 is depicted as comprising two separate semicircular segments with overlapping chord edges 93 to facilitate removal of the liner 92 from the film 52.

As described above, a sensor unit 12 can be placed in the cavity 46 of the carrier 44 by peeling the closure assembly 58 away from the outer cover layer 48 to expose the cavity 46, placing the sensor unit 12 on the lower foam member 61 within the cavity 46, and then closing the cavity 46 by reapplying the closure assembly 58, such that the nonpermanent adhesive element 63 re-adheres the closure assembly 58 to the outer cover layer 48. In doing so, the upper foam member 62 of the closure assembly 58 is pressed against the upper side of the sensor unit 12, and the lower and upper foam members 61 and 62 compressively secure the sensor unit 12 therebetween as depicted in FIG. 7A. Once the dressing assembly 10 has been applied to a patient's skin 56 and adhered thereto with the skin-adhesive film 52, the sensor unit 12 remains separated from the skin 56 by the lower foam member 61 and the skin-adhesive film 52, and the thicker padding provided by the annular-shaped foam member 60 disperses pressure surrounding the sensor unit 12.

From the above description, it can be appreciated that alternative methods of using the dressing assembly 10 include its use without a sensor unit 12. For example, the carrier 44 can be used alone to protect a region of a patient's skin 56 and, if present, a pre-existing wound 66 as depicted in FIG. 7B. As another example, the closure assembly 58 can be completely removed and, optionally, the central portion of the skin-adhesive film 52 surrounded by the perforations 52a can be removed to create a through-hole in the dressing assembly 10 so that when the dressing assembly 10 is applied to the skin 56 of a patient, a wound 66 is exposed within the through-hole as shown in FIG. 7C. In each of these examples, the thick padding provided by the annular-shaped foam member 60 disperses pressure to regions of the skin 56 surrounding the wound 66 within the through-hole, enabling the dressing assembly 10 to protect the wound 66 from pressure that might otherwise lead to pressure ulcers. The through-hole within the dressing assembly 10 also allows for the application of medications to the wound 66 exposed within the through-hole.

Figure 9:
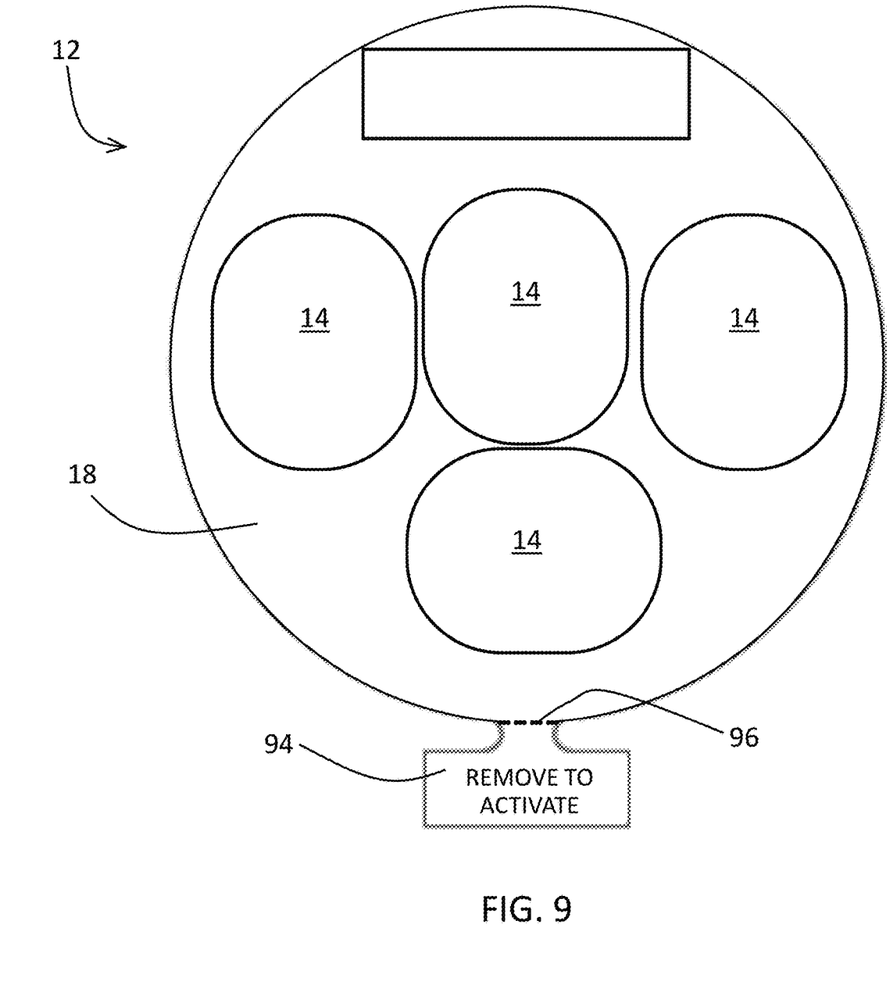
FIGS. 9 and 10 schematically represent, respectively, plan and cross-sectional views of a sensor unit suitable for use with the dressing assemblies of FIGS. 1 through 8.
Figure 10:
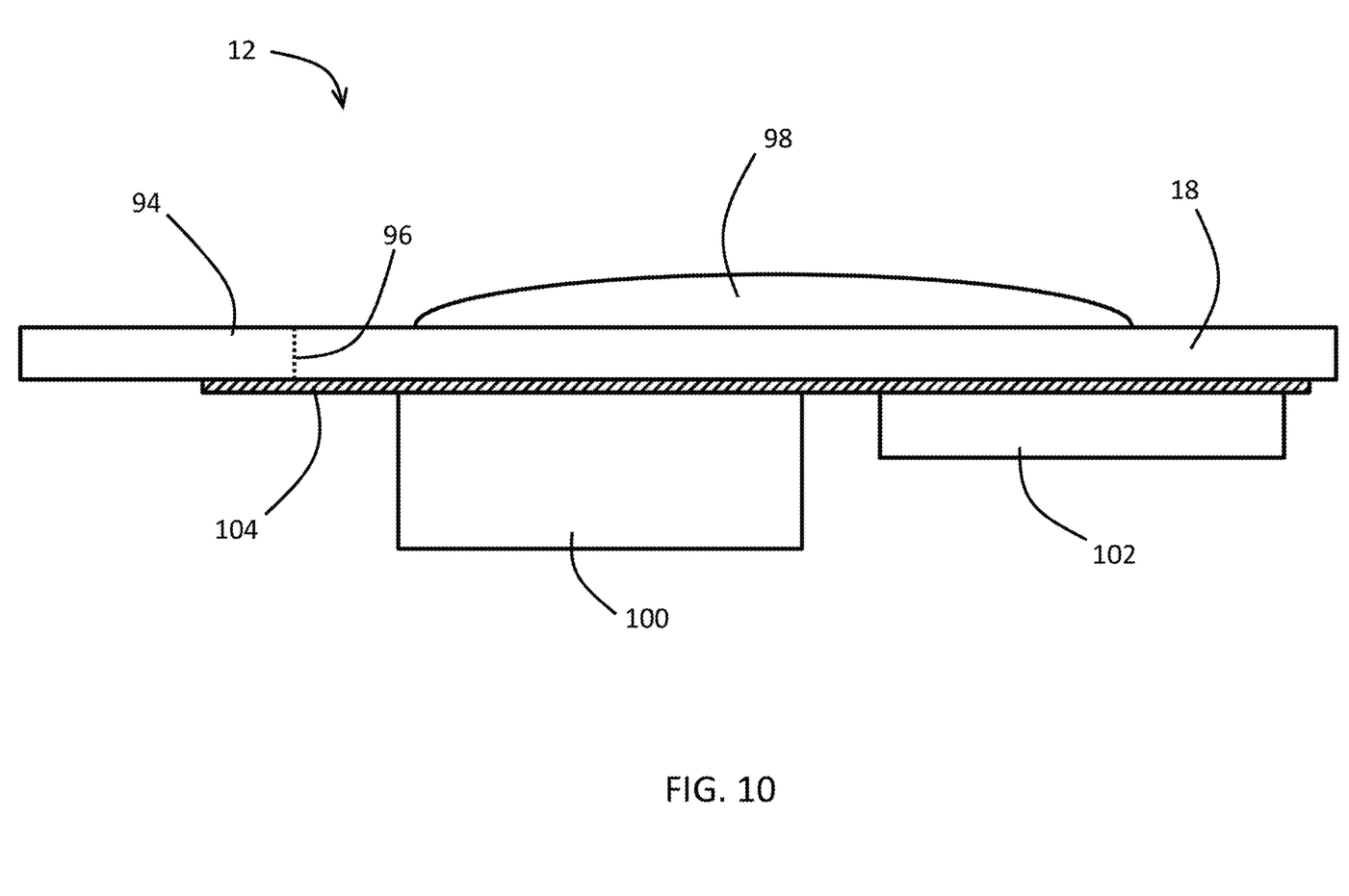

FIGS. 9 and 10 schematically represent a particular but nonlimiting embodiment of the sensor unit 12. FIG. 9 schematically represents multiple transducers 14 (at least one of which is a pressure-sensitive transducer) mounted to the substrate 18 of the sensor unit 12 In FIG. 10, which represents a cross-sectional view of the unit 12, the transducers 14 are represented as enclosed by a flexible but protective cover 98 on the substrate 18, and a battery 100, a Bluetooth low energy (Bluetooth LE, or BLE) radio module 102, and electrical circuitry 104 on the opposite side of the substrate 18. The substrate 18 includes a break-off tab 94 that projects from an adjacent edge of the substrate 18. The break-off tab 94 is delineated with a line of weakness, in this example, perforations 96 that separate the tab 94 from the remainder of the substrate 18. A portion of the electrical circuitry 104 extends onto the tab 94 so that power from the battery 100 is not delivered to the radio module 102 while the tab 94 remains attached to the substrate 18, but removal of the tab 94 and that portion of the electrical circuitry 104 on the tab 94 initiates the supply of power from the battery 100 to the radio module 102, thus activating the sensor unit 12. The tab 94 projects a sufficient distance from the periphery of the substrate 18 to prevent the placement of the sensor unit 12 within the cavity 46 of the dressing assembly 10, so that removal of the tab 94 and, consequently, activation of the sensor unit 12 is required before installing the sensor unit 12 in the dressing assembly 10.

While the invention has been described in terms of specific embodiments, it is apparent that other forms could be adopted by one skilled in the art. For example, the dressing assemblies 10 and their components could differ in appearance and construction from the embodiments shown in the drawings, the functions of each component could be performed by components of different construction but capable of a similar (though not necessarily equivalent) function, and various materials and assembly, calibration and test procedures could be used in the manufacture and setup of the dressing assembly 10. Other options include the use of various different pressure measurement modalities (including variable output pressure sensors), and the use of any number of different geometric configurations of dressing assemblies 10 beyond an oval or round configuration. Different sensor technologies can be incorporated into the dressing assemblies 10 to measure a range of specific pressures, and a variety of different sensors may be used to measure, among other things, temperature, pressure, moisture, capillary flow, skin resistivity and other biological indicators. The dressing assemblies 10 can be used in monitoring systems configured for use by patients in medical facilities or at home, as well as patients restricted to wheelchairs, ambulatory patients, etc.

Accordingly, it should be understood that the invention is not limited to the specific embodiments illustrated in the drawings. It should also be understood that the phraseology and terminology employed above are for the purpose of disclosing the illustrated embodiments, and do not necessarily serve as limitations to the scope of the invention. Therefore, the scope of the invention is to be limited only by the following claims.

The invention claimed is:

1. A wireless pressure-sensitive dressing assembly adapted to be applied to a surface of a patient's body that is susceptible to damage from soft tissue pressure, the wireless pressure-sensitive dressing assembly comprising:
   a carrier comprising:
      a skin-adhesive film;
      an outer cover layer overlying and adhered to the skin-adhesive film comprising a central aperture therethrough;
      an annular-shaped foam member between the skin-adhesive film and the outer cover layer, the annular-shaped foam member having a cavity defined therein;
      a lower foam member located within the cavity adjacent a portion of the skin-adhesive film; and
      a closure assembly overlying the central aperture of the outer cover layer, the closure assembly comprising a nonpermanent adhesive element that releasably adheres the closure assembly to the outer cover layer to enable the closure assembly to selectively close and selectively expose the cavity, the closure assembly comprising an upper foam member that extends through the central aperture of the outer cover layer and is disposed in the cavity when the closure assembly releasably closes the cavity; and
   a sensor unit removably secured within the cavity and compressed between the lower and upper foam members, the sensor unit generating electrical outputs corresponding to soft tissue pressure sensed by the wireless pressure-sensitive dressing assembly at the surface of the patient's body.

2. The wireless pressure-sensitive dressing assembly according to claim 1, wherein the sensor unit comprises a radio module configured to wirelessly transmit the electrical outputs from the sensor unit to a tablet, a smartphone, a gateway, a server or a wireless converter box that is physically separate from the wireless pressure-sensitive dressing assembly.

3. The wireless pressure-sensitive dressing assembly according to claim 1, wherein the closure assembly comprises a grip tab by which the nonpermanent adhesive element can be overcome to expose the cavity.

4. The wireless pressure-sensitive dressing assembly according to claim 1, wherein the outer cover layer and the skin-adhesive film are adhered to define a periphery of the carrier.

5. The wireless pressure-sensitive dressing assembly according to claim 4, wherein the periphery of the carrier is circular or oval.

6. The wireless pressure-sensitive dressing assembly according to claim 4, wherein the periphery of the carrier has radial slits therein.

7. The wireless pressure-sensitive dressing assembly according to claim 1, wherein the lower foam member and a portion of the skin-adhesive film underlying the lower foam member are removable so that the cavity defines a through-hole within the carrier.

8. The wireless pressure-sensitive dressing assembly according to claim 7, wherein the portion of the skin-adhesive film is surrounded by a perforation to enable removal thereof from the carrier.

9. The wireless pressure-sensitive dressing assembly according to claim 1, wherein the sensor unit comprises a substrate, a battery and a radio module mounted on the substrate, a break-off tab that extends from an edge of the substrate with perforations separating the break-off tab from a remainder of the substrate, and electrical circuitry having a portion that extends onto the break-off tab, the electrical circuitry being configured so that power from the battery is not delivered to the radio module while the break-off tab remains attached to the substrate, and so that removal of the break-off tab and the portion of the electrical circuitry on the break-off tab initiates supply of power from the battery to the radio module and activation of the sensor unit.

10. The wireless pressure-sensitive dressing assembly according to claim 9, wherein the break-off tab projects a sufficient distance from a periphery of the substrate to prevent placement of the sensor unit within the cavity of the dressing assembly, and removal of the break-off tab and, consequently, activation of the sensor unit are required before the sensor unit can be placed in the cavity of the dressing assembly.

11. A method of monitoring a plurality of sensed output signals and providing a warning to a patient or caregiver that the patient needs attention, the method comprising:
   applying a wireless pressure-sensitive dressing assembly to a surface of the patient's body, the wireless pressure-sensitive dressing assembly comprising a carrier comprising a skin-adhesive film, an outer cover layer overlying and adhered to the skin-adhesive film comprising a central aperture therethrough, an annular-shaped foam member between the skin-adhesive film and the outer cover layer, a cavity defined within the annular-shaped foam member, a lower foam member located within the cavity adjacent a portion of the skin-adhesive film, and a closure assembly overlying the central aperture of the outer cover layer, the closure assembly comprising a nonpermanent adhesive element that releasably adheres the closure assembly to the outer cover layer to enable the closure assembly to selectively close and selectively expose the cavity, the closure assembly comprising an upper foam member that extends through the central aperture of the outer cover layer and is disposed in the cavity when the closure assembly releasably closes the cavity;
   exposing the cavity with the closure assembly;
   placing a sensor unit within the cavity and closing the cavity with the closure assembly to compress the sensor unit between the lower and upper foam members;
   generating electrical outputs with the sensor unit corresponding to soft tissue pressure sensed by the sensor unit at the surface of the patient's body;
   monitoring the electrical outputs generated by the sensor unit; and
   generating an alert if the electrical outputs exceeds a threshold level.

12. The method according to claim 11, further comprising wirelessly transmitting the electrical outputs from a radio module of the sensor unit to a tablet, a smartphone, a gateway, a server or a wireless converter box that is physically separate from the wireless pressure-sensitive dressing assembly.

13. The method according to claim 11, wherein the closure assembly comprises a grip tab and the method comprises using the grip tab to overcome the nonpermanent adhesive element and expose the cavity.

14. The method according to claim 11, wherein the outer cover layer and the skin-adhesive film are adhered to define a periphery of the carrier.

15. The method according to claim 14, wherein the periphery of the carrier is circular.

16. The method according to claim 14, wherein the periphery of the carrier is oval, the method comprising applying the carrier as a sacral dressing over a sacrum of the patient.

17. The method according to claim 14, wherein the periphery of the carrier has radial slits, the method comprising applying the carrier over a bony prominence of the patient.

18. The method according to claim 11, the method comprising removing the lower foam member and a portion of the skin-adhesive film underlying the lower foam member so that the cavity defines a through-hole within the carrier.

19. The method according to claim 11, wherein the sensor unit comprises a substrate, a battery and a radio module mounted on the substrate, a break-off tab that extends from an edge of the substrate with perforations separating the break-off tab from a remainder of the substrate, and electrical circuitry having a portion that extends onto the break-off tab, the method comprising removing the break-off tab and the portion of the electrical circuitry on the break-off tab to initiate supply of power from the battery to the radio module and activate the sensor unit.

* * * * *